United States Patent
Breedvelt-Schouten (10) Patent No.: US 11,094,063 B2
(45) Date of Patent: *Aug. 17, 2021

(54) BRUSHING APPARATUS FOR PHYSICAL ANOMALY DETECTION

(71) Applicant: International Business Machines Corporation, Armonk, NY (US)

(72) Inventor: Ilse M. Breedvelt-Schouten, Manotick (CA)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/443,247

(22) Filed: Jun. 17, 2019

(65) Prior Publication Data

US 2020/0394799 A1 Dec. 17, 2020

(51) Int. Cl.
| | |
|---|---|
| A46B 15/00 | (2006.01) |
| G06T 7/00 | (2017.01) |
| G06T 7/13 | (2017.01) |
| H04N 5/225 | (2006.01) |
| A61B 5/00 | (2006.01) |
| A45D 24/10 | (2006.01) |

(52) U.S. Cl.
CPC .......... *G06T 7/0014* (2013.01); *A45D 24/10* (2013.01); *A46B 15/0006* (2013.01); *A61B 5/0064* (2013.01); *A61B 5/0077* (2013.01); *A61B 5/746* (2013.01); *G06T 7/13* (2017.01); *H04N 5/2253* (2013.01); *A46B 2200/104* (2013.01); *G06T 2207/30088* (2013.01)

(58) Field of Classification Search
CPC ..... G06K 9/00664; G06T 7/0014; G06T 7/13; G06T 2207/30088; A45D 24/10; H04N 5/2253; H04N 5/2256; H04N 7/188
USPC ........................................................... 348/77
See application file for complete search history.

(56) References Cited

U.S. PATENT DOCUMENTS

| | | | |
|---|---|---|---|
| 8,139,858 B1 | 3/2012 | Landwehr | |
| 2015/0148684 A1* | 5/2015 | Baym | A61B 5/0071 600/476 |
| 2015/0164213 A1* | 6/2015 | Hyde | A46B 15/0055 600/301 |
| 2018/0027948 A1* | 2/2018 | Troy | A45D 24/30 |
| 2018/0046872 A1 | 2/2018 | Diamond | |

FOREIGN PATENT DOCUMENTS

WO 9966790 A1 12/1999

OTHER PUBLICATIONS

"Anomaly Detection," Fast AI Forums, Dec. 2016, 3 pages. <https://forums.fast.ai/t/anomaly-detection/283>.

(Continued)

*Primary Examiner* — Ayman A Abaza
(74) *Attorney, Agent, or Firm* — Brian D. Welle (57) ABSTRACT

A method for monitoring and detecting physical anomalies may include receiving, by a processor and from a camera of a brushing apparatus, an image of a body from a predetermined distance away from the body. The method may further include detecting, by the processor, an atypical contour of the image that indicates a physical anomaly. The method may further include generating, by the processor, a notification in response to detecting the atypical contour that indicates the physical anomaly.

19 Claims, 4 Drawing Sheets

(56) References Cited

OTHER PUBLICATIONS

"DeepLearning Anomaly Detection for Images," StackOverflow.com, Apr. 16, 2017, 3 pages. <https://stackoverflow.com/questions/43441396/deeplearning-anomaly-detection-for-images>.

"How to Tick Check Yourself," After Gadget, Oct. 4, 2011, 7 pages. <https://aftergadgetwordpress.com/2011/10/04/how-to-tick-check-yourself/>.

"What to Do After a Tick Bite," Johns Hopkins Lyme Disease Research Center, Feb. 27, 2019, 2 pages. <https://www.hopkinslyme.org/lyme-education/what-to-do-after-a-tick-bite/>.

Barbedo et al., "The use of infrared images to detect ticks in cattle and proposal of an algorithm for quantifying the infestation," Veterinary Parasitology, 235, 106-112, Jan. 2017, 20 pages. <https://www.researchgate.net/publication/312649237_The_use_of_infrared_images_to_detect_ticks_in_cattle_and_proposal_of_an_algorithm_for_quantifying_the_infestation>.

Breedvelt-Schouten, "Physical Anomaly Detection," U.S. Appl. No. 16/443,189, filed Jun. 17, 2019.

List of IBM Patents or Patent Applications Treated as Related, Jun. 17, 2019, 2 pages.

Mallick, "Image Recognition and Object Detection : Part 1," LearnOpenCV.com, Nov. 14, 2016, 8 pages. <https://www.learnopencv.com/image-recognition-and-object-detection-part1/>.

Worland, "Health Officials Are Warning This Tick Season Could Be the Worst Yet," Time.com, May 19, 2017, 3 pages. <https://time.com/4781678/ticks-lyme-diseaseclimate-change/>.

\* cited by examiner

BRUSHING APPARATUS FOR PHYSICAL ANOMALY DETECTION

BACKGROUND

Ticks are carriers of Lyme disease. With the recent increase of tick infestations in the world, more and more people may be at risk for Lyme disease. One of the best ways to prevent Lyme disease is to identify any ticks present on your skin and to then carefully remove these ticks. If left on long enough to start feeding, ticks may transfer Lyme disease. However, ticks can be very small, as small as 0.5 mm. Given that ticks tend to like hiding in areas near hair, it may be difficult or impossible for a person to check every portion of a body, particularly their own body.

SUMMARY

Aspects of the present disclosure relate to a method, system, and computer program product relating to detecting physical anomalies on a body. For example, the method may include receiving, by a processor and from a camera of a brushing apparatus, an image of a body from a predetermined distance away from the body. The method may further include detecting, by the processor, an atypical contour of the image that indicates a physical anomaly. The method may further include generating, by the processor, a notification in response to detecting the atypical contour that indicates the physical anomaly.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Aspects of the present disclosure relate to detecting physical anomalies, and more particular aspects relate to using one or more cameras of a brushing device that have a depth of field length that is substantially similar to bristles of the brush such that the camera may be used to detect physical anomalies while the brush is brushing a body. While the present disclosure is not necessarily limited to such applications, various aspects of the disclosure may be appreciated through a discussion of various examples using this context.

Conventional systems and methods may have one or more disadvantages in detecting physical anomalies. Physical anomalies may include relatively small objects (e.g., smaller than a centimeter) that may be visually observable on the skin of a person that may be undesired by that person, such as ticks, lice, other insects, malignant moles, or the like. As discussed above in the background, ticks are carriers of serious diseases such as Lyme disease. Further, it may be difficult or even impossible for some users to find ticks that are on a body, particular if a person is trying to find a tick on themselves. In some examples, a user may try to find a tick using a brush or the like, but—particularly in the dark—it may be extremely difficult to locate a tick that may be as small as 0.5 millimeters among hairs that may be as thick as 0.12 millimeters.

Aspects of this disclosure relating to incorporating one or more lights and cameras into a brushing apparatus to capture images of the body and detect if ticks or other physical anomalies are present on a body. In addition to ticks, other insects such as lice or moles of changing size or the like may be detected. A computing system that includes a memory that stores instructions for detecting physical anomalies and a processor communicatively coupled to the memory may detect physical anomalies as described herein. For example, this computing system (hereinafter referred to as a computing controller, or as a controller) may compare the images gathered by the camera(s) to stored contours to identify if any of the images include unexpected contours. Contours may include shapes of physical objects that are identified on a body. As discussed herein, unexpected contours may include shapes other than hair and musculature and bone structure and the like. In some examples, moles may be included in unexpected contours.

The controller may compare these unexpected contours to stored composite contours of injurious items (e.g., ticks) and to stored historical contours associated with the user (e.g., such as moles or scars) or the like to identify unexpected contours. As used herein, a composite contour may relate to a contour that was created from two or more contours that have been merged and/or averaged together to become relatively more universal (e.g., rather than distinct to a specific physical anomaly). Once the controller matches the unexpected contour to such a stored contour in a way that indicates a potential physical anomaly, the controller may notify the user of this detected contour in a notification that includes the gathered picture of the unexpected contour. In response to the user agreeing with the identification, the algorithm used by the controller to identify this physical anomaly is reinforced, such that similarly shaped contours may be similarly identified in the future. Conversely, where the user disagrees and corrects and/or disregards the provided identification, the controller may update the algorithm with altered or deleted or additional contours as per the correction from the user.

Figures 1A, 1B, 1C:
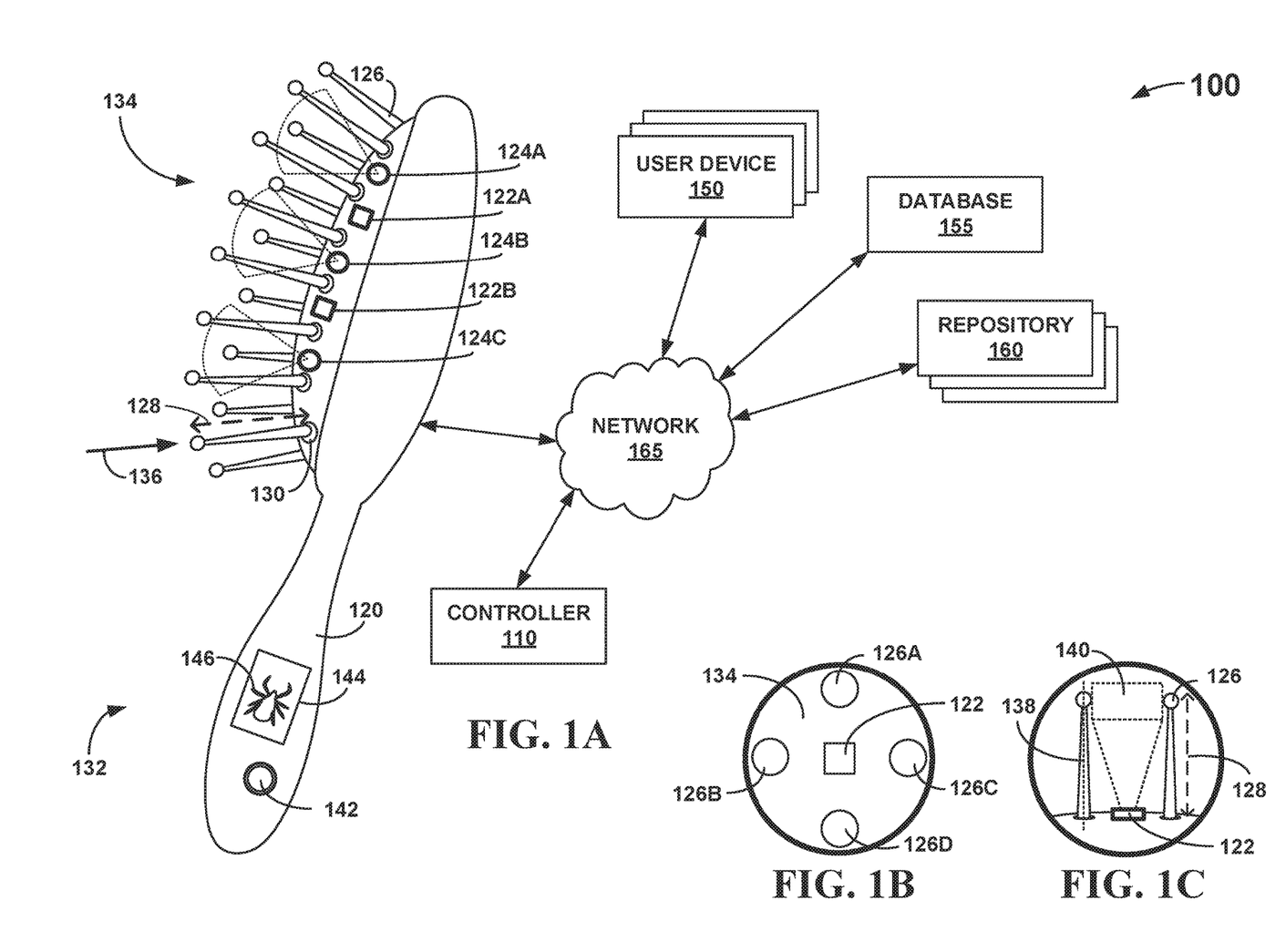
FIG. 1A depicts a conceptual diagram of an example system in which a controller detects physical anomalies with a brushing apparatus.
FIG. 1B depicts a conceptual illustration of an example detail view of the brushing apparatus of FIG. 1A as viewed along a longitudinal axis of bristles of the brushing apparatus.
FIG. 1C depicts a conceptual illustration of an example detail view of a depth of field of a camera of a brushing apparatus of FIG. 1A as viewed perpendicular to a longitudinal axis of bristles of the brushing apparatus.

For example, FIG. 1A depicts system 100 that includes controller 110 that is configured to detect physical anomalies. Controller 110 may include a computing device, such as computing device 200 of FIG. 3 that includes a processor communicatively coupled to a memory that includes instructions that, when executed by the processor, cause controller 110 to execute the operations described below. Controller 110 may detect physical anomalies using brushing apparatus 120. Brushing apparatus 120 may include head 134 and handle 132 that extends away from head 134. Though controller 110 is depicted as external to brushing apparatus 120 for purposes of illustration, in some examples controller 110 may be integrated and/or embedded into brushing apparatus 120 (e.g., integrated or embedded or formed into head 134 and/or handle 132 of brushing apparatus 120). In such examples, controller 110 may be embedded into brushing apparatus 120 in a pseudo-permanent fashion that it may be difficult or impossible to remove controller 110 from brushing apparatus 120 without damaging or destroying one or both of controller 110 and/or brushing apparatus 120. In other such examples, controller 110 may be embedded into brushing apparatus 120 such that controller 110 may be easily detachable from brushing apparatus 120.

Where controller 110 is external to brushing apparatus 120 as depicted in FIG. 1A, controller 110 may monitor for and detect physical anomalies using brushing apparatus 120 by communicating with brushing apparatus 120 over network 165. Network 165 may include a computing network over which computing messages may be sent and/or received. For example, network 165 may include the Internet, a local area network (LAN), a wide area network (WAN), a wireless network such as a wireless LAN (WLAN), or the like. Network 165 may comprise copper transmission cables, optical transmission fibers, wireless transmission, routers, firewalls, switches, gateway computers and/or edge servers. A network adapter card or network interface in each computing/processing device (e.g., controller 110, user devices 150, and/or database 155) may receive messages and/or instructions from and/or through network 165 and forward the messages and/or instructions for storage or execution or the like to a respective memory or processor of the respective computing/processing device.

Though network 165 is depicted as a single entity in FIG. 1A for purposes of illustration, in other examples network 165 may include a plurality of private or public networks. For example, controller 110 and database 155 may communicate together over a private LAN of network 165. Additionally, controller 110 may communicate with repositories 160 over a public portion of network 165 using the Internet.

Head 134 may include a plurality of bristles 126. The relative size and arrangement of head 134, handle 132, and bristles 126 (as well as the depicted number of bristles 126) in FIG. 1A is depicted for purposes of illustration only, as controller 110 may be configured to detect physical anomalies for brushing apparatus 120 with any size and arrangement of head 134, handle 132, and bristles 126 (as well as any number of bristles 126) that is consistent with this disclosure. For example, though brushing apparatus 120 is depicted with relatively sparse bristles 126 that are spaced relatively widely apart for the sake of illustration, in some examples brushing apparatus 120 may far more bristles 126, such as dozens of bristles 126, where such bristles 126 are space relatively closely together. For another example, though handle 132 is depicted as a single piece in FIG. 1A for purposes of clarity, in other examples handle 132 may be extendable through a telescope action or the like. Configuring handle 132 to be extendable may improve an ability of a user to reach substantially all of a body (e.g., such as all of their own body) with brushing apparatus 120.

Further, though bristles 126 are depicted as having a relatively broad base and narrowing as bristles 126 extend along a longitudinal axis toward a terminal bulb, this shape is depicted for purposes of illustration only. Bristles 126 may be any shape that is consistent with this disclosure. For example, bristles 126 may define a substantially constant outer diameter as bristles 126 extend away from head 134 along their longitudinal axis (e.g., longitudinal axis 138 of FIG. 1C).

Brushing apparatus 120 may further include one or more cameras 122A, 122B (hereinafter collectively referred to as "cameras 122" and generically referred to as "camera 122"). Cameras 122 may be secured to head 134 adjacent bristles 126. Though two cameras 122 are depicted in FIG. 1A for purposes of illustration, it is to be understood that more or less cameras 122 may be in brushing apparatus 120 in other examples. Further, though cameras 122 are depicted as boxes in FIG. 1A, again for purposes of illustration, cameras 122 may be any shape and size so long as cameras are configured to gather images consistent with this disclosure.

Brushing apparatus 120 may be configured to improve an ability of cameras 122 to capture images of potential anomalies on the skin of a body that brushing apparatus 120 is brushing. For example, cameras 122 may be secured to head 134 adjacent to bristles 126 such that bristles 126 may part hair of a body to give cameras 122 a relatively unobstructed path to the skin of a body. Toward this end, though FIG. 1A depicts cameras 122 without bristles on a "near side" of cameras 122 for purposes of illustration (to better depict cameras 122), in some examples bristles 126 may substantially surround camera 122. FIG. 1B depicts an example detail view of camera 122 and four bristles 126A-126D (collectively referred to as "bristles 126") as viewed along longitudinal axis of bristles 126. As depicted, camera 122 may be secured to head 134 such that camera 122 is equidistant between four equally spaced apart bristles 126. Further, as depicted, camera 122 and bristles 126 may be secured to head 134 such that there is a respective bristle adjacent to substantially each side of camera 122 (e.g., such that bristles 126 are arranged on a circle around camera 122 spaced 90° apart). By locating bristles 126 on many or all or each side of camera 122, bristles 126 may be relatively more likely to part a path among hair of a body to give camera 122 a relatively unobstructed path to the skin of the body, no matter which direction brushing apparatus 120 may be moving.

Further, camera 122 and bristles 126 may be configured to improve an ability of camera 122 to focus on objects near or on the skin of a body when brushing apparatus 120 is brushing a body. For example, FIG. 1C depicts an example detail view of brushing apparatus 120 as viewed perpendicular to longitudinal axis 138 of bristles 126. As depicted in FIG. 1C, camera 122 may define depth of field 140 (e.g., a distance away from camera 122 upon which one or more lenses of camera 122 are focused and may therein capture images with good clarity) around longitudinal length 128 of bristles 126. As understood by one of ordinary skill in the art, camera 122 may define depth of field 140 by, e.g., relative internal distances between a lens of camera 122 and a light-reacting sensor of camera 122.

Camera 122 may be configured to have depth of field 140 that is substantially similar to longitudinal length 128 of bristles 126. Put differently, camera 122 may define depth of field 140 such that depth of field 140 includes longitudinal length 128 and extends past and/or is shorter than longitudinal length 128. For example, camera 122 may be configured to define depth of field 140 that extends from a length that is slightly longer than longitudinal length 128 of bristles 126 to a length that is slightly shorter than longitudinal length 128. For example, where bristles 126 define longitudinal length 128 that is two centimeters long, depth of field 140 may include a depth of 0.8 centimeters starting from 1.6 centimeters away camera 122 and extending to a maximum length away from camera 122 of 2.4 centimeters. Camera 122 may be configured to define depth of field 140 such that substantially all anomalies are within it when bristles 126 are engaged with skin of a body (e.g., engaged with at least compression force 136 as described herein).

Turning back to FIG. 1A, bristles 126 may be configured to be substantially unbending and uncompressing in response to compressive force 136 that is imparted on bristles 126 toward head 134. Compression force 136 may be the force at which a human may press a brush such as brushing apparatus 120 up against their head when brushing their hair. The shape of bristles 126 may configure bristles 126 to be resistant to bending and/or compressing (e.g., such that bristles 126 may compress no more than 1 millimeter or so in response to compression force 136). For example, bristles 126 may have an outer diameter that is thick enough to resist bending and/or compressing. Further, a material of bristles 126 may be selected to configure bristles 126 to be relatively resistant to bending and/or compressing, such that bristles 126 may substantially not compress (e.g., not compress more than a nominal amount) in response to compression force 136. For example, bristles 126 may be made of a material such as nylon, high-density polyethylene (HDPE), or the like that has relatively high tensile strength and therein is relatively resistant to bending and/or compressing as described herein.

As a result of bristles 126 being configured to be relatively resistant to bending and/or compressing, bristles 126 may be configured to define a relatively static longitudinal length 128 during engagement with (e.g., when brushing apparatus 120 is used to brush) a body. As a result of bristles 126 defining a relatively static longitudinal length 128, brushing apparatus 120 may increase a likelihood of anomalies being within depth of field 140 during operation of brushing apparatus 120. In this way, images being received by controller 110 may always be a predetermined distance away the object of the images. Computing systems in general may be better at analyzing images from a fixed perspective and/or distance rather than from a varying distance. As such, enabling a processor of controller 110 to analyze images from this predetermined distance may improve an ability of controller 110 to monitor for and identify physical anomalies.

Brushing apparatus 120 may include one or more lights 124A-124C (collectively referred to as "lights 124" and generically referred to as "light 124"). Similar to cameras 122, the specific number and arrangement of lights 124 is depicted in FIG. 1A is for purposes of illustration only, as any number and arrangement of lights 124 that is consistent with this disclosure is possible. Lights 124 may include light emitting diodes (LEDs) in some examples, though in other examples other types of lights (e.g., halogen, compact fluorescent, incandescent) may be used. Lights 124 may be configured to output a cone or beam of light as depicted in FIG. 1A to illuminate an area. Lights 124 may be configured to illuminate an area that overlaps with depth of field 140 of camera 122. For example, lights 124 may be selected to output an amount of lumens that is required to provide sufficient light for cameras 122 to capture images that can include unexpected contours. Lights 124 may be adjacent cameras 122 to best illuminate this area. In this way, lights 124 may be configured to improve an ability of cameras 122 to capture images of physical anomalies.

Brushing apparatus 120 may include power button 142 or the like for turning on brushing apparatus 120. Specifically, turning on brushing apparatus 120 using power button may cause a power supply (not depicted) to provide power to components (e.g., cameras 122, lights, 124, pressure sensors 130) to provide their respective functionality as described herein. This power supply may include a battery, an alternating current (A/C) plugin (e.g., to plug brushing apparatus 120 into a wall plugin), or the like. Turning on brushing apparatus 120 using power button 142 may cause and/or enable lights 124 to turn on and/or cameras 122 to capture images.

Power button 142 may be configured to be relatively difficult to accidentally turn on, such that it may require a purposeful action by a user to turn on brushing apparatus 120. For example, power button 142 may include a depressible button that is configured to turn on brushing apparatus 120 in response to being depressed to a depth (e.g., three millimeters) by a relatively strong downward force exerted by a single finger (e.g., 15 newtons of force), such that it is relatively unlikely that brushing apparatus 120 would be turned on by, e.g., jostling around within a backpack. Further, by configuring brushing apparatus 120 such that brushing apparatus 120 includes a power supply to toggle power to camera 122, lights 123, pressure sensors 130, or the like, brushing apparatus 120 may be configured to avoid capturing images in response to bristles 126 being depressed in response to incidental use (e.g., brushing apparatus 120 jostling around within a backpack).

Brushing apparatus 120 may include pressure sensors 130 at an intersection of bristles 126 and head 134. Pressure sensors 120 may be configured to detect when compression force 136 exceeds a threshold force, indicating that bristles 126 are engaged with a body. The threshold force may be a force that a user substantially always exerts when brushing their body with brushing apparatus 120, such as between 20 and 30 newtons of force. In some examples, this threshold force may be customizable, as different users may engage a body with brushing apparatus 120 with a different amount of force.

Controller 110 may identify when pressure sensors 130 detect that bristles 126 are being pressed in with compression force 136 that exceeds a threshold force. In some examples, controller 110 may cause lights 124 to turn on and/or cause camera 122 to capture images in response to identifying that pressure sensors 130 detect compression force 136 that exceeds the threshold force. In certain examples, controller 110 may only be configured to turn on lights 124 and/or cause camera 122 to capture images once power button 142 has turned on.

When brushing apparatus 120 is in operation (e.g., bristles 126 engaged with skin of a body with at least compression force 136), controller 110 may analyze images captured by cameras 122. In some examples, cameras 122 may capture a video feed, such that controller 110 may analyze many or substantially all frames of the video feed. Controller 110 may determine whether images captured by cameras 122 include any unexpected contours. As used herein, unexpected contours may include discolorations or shapes of the image that are not identified to be hair or muscle or bone structure or the like of the body.

Figure 3:
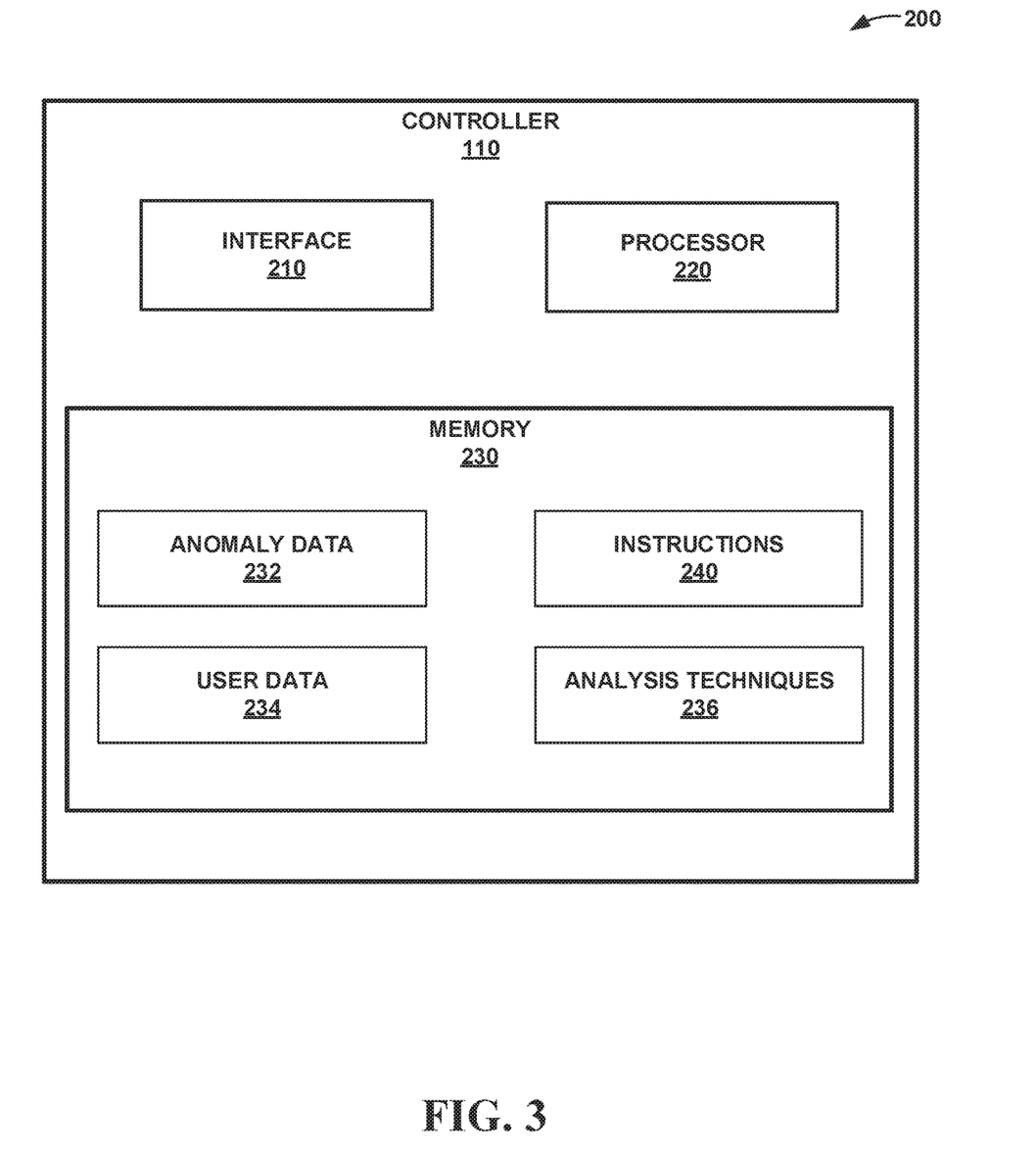
FIG. 3 depicts a conceptual box diagram of a computing system that may be configured to detect physical anomalies using a brushing apparatus.

If controller 110 detects any unexpected contours, controller 110 compares these unexpected contours against data of database 155, which may be a computing device as described herein. For example, database 155 may include a server or a rack of servers or a laptop or a desktop or the like. Controller 110 may access database 155 over network 165. Though database 155 is depicted as a separate device from controller 110 for the sake of illustration, in other examples database 155 may be integrated into controller (e.g., as depicted in FIG. 3).

Database 155 may include composite contours of physical anomalies (e.g., such as ticks or lice or fleas), historical contours of features of the user such as moles or scars, or the like. If controller 110 detects that a detected unexpected contour matches a composite contour, controller 110 may send a notification to one or more user devices 150. User devices 150 may be computing devices such as those described herein that are associated with a user. For example, user devices 150 may include cell phones or laptops or the like. Controller 110 may send the notification to user devices 150 over network 165 using the Internet, using a Bluetooth connection, using near-field communication, or the like. The notification as received by user device 150 may include a pop-up message, text message, email, notification within an application downloaded on user device 150, or the like.

The notification as sent to user devices 150 may include the images that included the unexpected contour. In some examples, the notification may include an ongoing video feed from cameras 122. A user may view the image(s) and decide if the unexpected contour matches the identified physical anomaly. For example, controller 110 may send a notification to user device 150 with an image that includes a contour that controller 110 has detected matches a composite contour of a tick. In this example, controller 110 may send the notification such that it includes text such as "Possible Tick Detection—Please confirm." In some examples, controller 110 may have tracking and/or directing a location of where on a body the tick is located. In such examples, controller 110 may provide a general and/or specific location of the tick or other physical anomaly within the notification.

In some examples, the notification may include details and/or an option to get details on how to respond to the physical anomaly. For example, the notification may include response tactics for how to remove a tick, and/or how to avoid future ticks, or the like. The notification may include this as text, a video, a link to an online source with this information, or the like.

A user may interact with user devices 150 to confirm and/or reject the classification of the unexpected contour as the physical anomaly (e.g., as a tick). Controller 110 may utilize machine learning techniques to update rules and contours and the like within database 155 using this feedback from user devices 150. For example, the user may see an image of a dirt smudge that controller 110 has identified as matching a contour of a tick. Controller 110 may receive this confirmation or rejection as sent by user using user device 150 over network 165.

In certain examples brushing apparatus 120 may include display 144. Display 144 may include a screen and/or an interactive interface (e.g., such as buttons or a touchscreen or keypad). In such examples, controller 110 may provide notifications to this screen rather than to user devices 150 such as described herein. For example, display 144 may generate image 146 that was most recently captured by camera 122, so that a user may immediately confirm and/or reject a classification as made by controller 110. In other examples (not depicted), display 144 may generate body and highlight or otherwise indicate a portion of body to engage with bristles 126. In this way, controller 110 may cause a plurality of data to be generated on display 144, such as further providing response tactics and the like directly on brushing apparatus 120. The user may be able to provide feedback directly to controller 110 using this interactive interface. For example, as described herein, a user may be able to provide confirmation or rejection to a match as provided by controller 110 using this interactive interface.

In examples where controller 110 receives a confirmation, controller 110 may strengthen a correlation between the composite contour and the physical anomaly on the body. In some examples, controller 110 may further tweak as possible the composite contour as stored within database 155 to better reflect the unexpected contour. Alternatively, where controller 110 receives a response from user device 150 that rejects the classification, controller 110 may weaken a correlation between the composite contour and the physical anomaly. For example, controller 110 may alter the composite contour to make it relatively less likely that contours similar to the unexpected contour may be identified as similar to the composite contour (and therein classified as a physical anomaly).

In other examples, controller 110 may determine that no contour of database 155 matches the unexpected contour with a degree of similarity above a threshold. In such examples, controller 110 may crawl through online repositories 160 (e.g., online forums or scientific catalogues or image collections) on network 165 to identify possible contours that match the unexpected contour and the like. For example, controller 110 may do a reverse image search of repositories 160 using the unexpected contour to identify contours of the repositories 160 that may match the unexpected contour.

If controller 110 identifies a contour of repositories 160 that matches the unexpected contour, controller 110 may execute natural language processing (NLP) techniques as discussed herein to identify the nature of the identified contour of the repository 160. For example, controller 110 may analyze image of the scientific catalogue in which the contour is identified to determine that the contour relates to an insect other than a tick as is already stored in database 155. Further, controller 110 may identify using NLP techniques that the identified contour relates to an anomaly that would feasibly be on the skin of a user. For example, if controller 110 matches the unexpected contour of the captured image with an identified contour of a grizzly bear, controller 110 may determine that it is relatively unlikely that a grizzly bear is currently within depth of field 140 of cameras 122, and may therein dismiss this match. In some examples, controller 110 may further identify response tactics as related to the identity of the identified contour. For example, where the identified contour is a kind of insect, the response tactics may include steps on how to remove the insect, identify if the insect has passed a condition or disease on to the user, and/or how to avoid the insect in the future.

If controller 110 identifies a contour of repositories 160 that matches the unexpected contour, controller 110 may generate a notification as described above with the captured image and the possible categorization as determined using NLP techniques on repositories. If controller 110 receives a positive confirmation from user devices 150 in response to this notification, controller 110 may create a new entry in database 155 with this new anomaly. Further, controller 110 may create a new composite contour by merging the unexpected contour and the identified contour from repositories 160. Alternatively, if controller 110 receives a negative response to the classification from user devices 150, controller 110 may dismiss this match. Additionally, controller 110 may make a new rule within database 155 that expressly rejects this match, such that controller 110 is relatively less like to match the identified contour with similar unexpected contours in the future.

In some examples, controller 110 may identify that no contour of database 155 and/or repositories 160 matched this unexpected contour. In such examples, controller 110 may send a notification to user devices 150 that indicates this unidentified contour. Controller 110 may receive a response from the user that identifies this contour. Additionally, or alternatively, controller 110 may receive a response from the user that indicates whether the unexpected contour is benign (e.g., does not indicate any concern) or injurious (e.g., indicates something of concern that warrants notifying a user in the future). In response to either, controller 110 may update database 155 accordingly to improve an ability of controller 110 to respond to similar unexpected contours in the future.

Figure 2A:
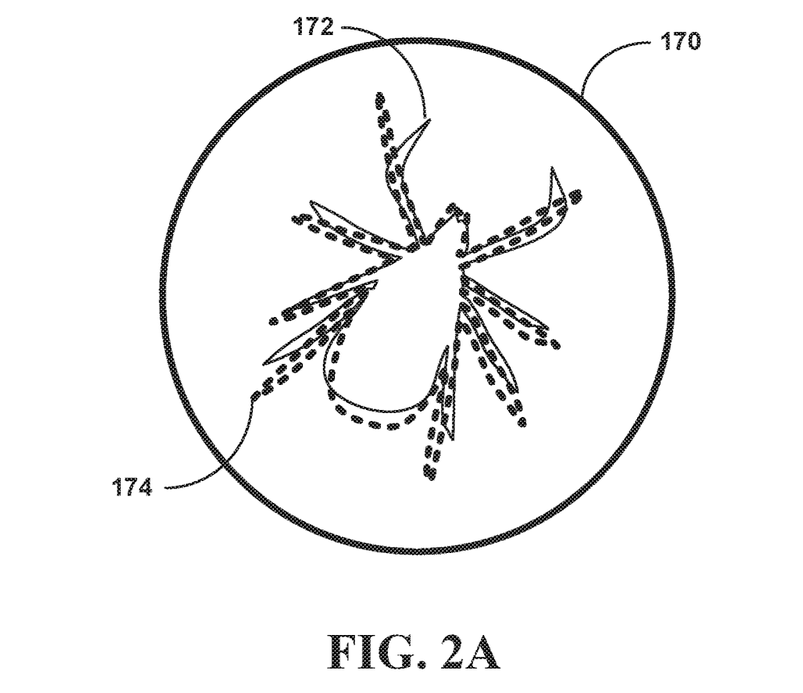
FIG. 2A depicts a conceptual illustration of a first example image that includes an atypical contour being compared to a composite contour of a physical anomaly of a tick.

For example, FIG. 2A depicts an example image 170 that is captured by cameras 122 of brushing apparatus 120. Controller 110 may identify unexpected contour 172 within image 170, which is depicted as a solid line in FIG. 2A. Controller 110 may compare this unexpected contour 172 against a plurality of contours of database 155 and identify that unexpected contour 172 is within a threshold similarity to composite contour 174 of a physical anomaly of a tick, which is depicted with a dotted line in FIG. 2A. For example, controller 110 may use pattern recognition techniques to identify that a general pattern of unexpected contour 172 is matched by composite contour 174 with a degree of accuracy that surpasses a threshold. Controller 110 may present image 170 (e.g., without composite contour 174) to user devices 150. In some examples, controller 110 may provide a video feed related to this unexpected contour 172, in case the user wants further visual information. Controller 110 may receive the confirmation from user device 150 that the image 170 contains unexpected contour 172 of a tick. In response to this, controller 110 may update composite contour 174 as applicable, such as by modifying the depicted front appendages to include a hooked shape.

Figure 2B:
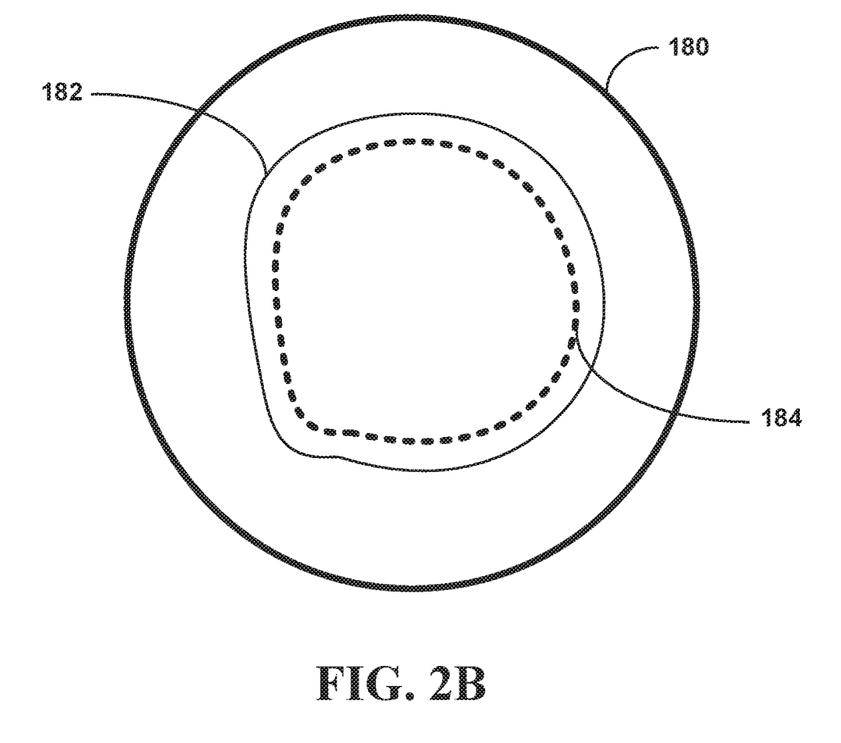
FIG. 2B depicts a conceptual illustration of a second example image that includes an atypical contour being compared to a historical contour of a physical anomaly of a mole.

In some examples, controller 110 may be configured to detect that something is an injurious physical anomaly as a result of an unexpected contour changing from a historical contour. For example, controller 110 may be configured to detect if a mole is changing size, indicating a possible melanoma. Further, in some examples controller 110 may initially notify a user regarding an unexpected contour indicating a mole of an atypical shape (e.g., not circular), color (e.g., not brown), and/or depth (e.g., not flat against the body) in a way that may indicate melanoma. In such examples, if user device 150 indicates that this shape, color, and/or depth is not injurious, controller 110 may disregard this mole going forward so long as a historical contour of the mole does not change size.

For example, FIG. 2B depicts an example image 180 of unexpected contour 182 of a mole. Controller 110 may compare this unexpected contour 182 with historical contour 184 of the same mole. As described herein, brushing apparatus 120 may be configured such that image 180 is taken from a same height as the initial image from which historical contour 184 was captured, such that a different size within image 180 indicates that the mole is changing size. For example, as described above, brushing apparatus 120 may be configured to maintain a relatively constant distance 128 from body across substantially all images captured by cameras 122 as a result of bristles 126 being configured to resist bending and/or compressing and as a result of pressure sensors 130 detecting compression force 136 as discussed herein, such that camera 122 only captures images when camera 122 is a substantially static distance away from anomalies.

Controller 110 may detect that unexpected contour 182 is a threshold percentage larger than historical contour 184. In some examples, the threshold percentage may be relatively low, such as 5% bigger, where an increased size may be classified as injurious. Controller 110 may send a notification to user devices 150 with image 180. In some examples, controller 110 may send image 180 with historical contour 184 provided as an overlapped image with unexpected contour 182, so that the user may compare a potential growth of the mole. If controller 110 receives feedback that the detected change is injurious, controller 110 may lower a threshold to detect injurious growth in the future. Conversely, if controller 110 receives feedback that the detected change is benign, controller 110 may increase a threshold to detect injurious growth in the future.

In some examples, a user may have a plurality of moles, such that controller 110 may utilize one or more techniques to tell different moles apart. For example, controller 110 may identify the unexpected contour 182 as matching the historical contour 182 as a result of the two contours matching a general shape. For another example, controller 110 may direct where a user is to brush with brushing apparatus 120, such that moles may be identified based on a predetermined location of those moles and then compared to their respective historical contours. For example, controller 110 may provide directions to user device 150. Directions may state to brush a first part of a scalp, then a second, then a first portion of a neck, then a second, etc., until the entire area that a user wants to monitor are brushed. As controller 110 directs the user, controller 110 may analyze detected moles with moles known to be in those location. Further, controller 110 may direct a user when to go over an area again, as controller 110 did not gain sufficient data from images from camera 122. Controller 110 may direct a user to brush many or all parts of a body, including limbs of a body.

Further, as discussed herein, a body may include both a human body and also bodies of other animals. For example, controller 110 may be configured to detect physical anomalies such as ticks on a dog or the like. In some such examples, bristles 126 may be relatively more numerous or head 134 may be relatively smaller or other such changes when brushing apparatus 120 is configured to detect physical anomalies on non-human animals.

As described above, controller 110 may include computing device 200 with a processor configured to execute instructions stored on a memory to execute the techniques described herein. For example, FIG. 3 is a conceptual box diagram of such computing device 200 of controller 110. While controller 110 is depicted as a single entity (e.g., within a single housing) for the purposes of illustration, in other examples, controller 110 may include two or more discrete physical systems (e.g., within two or more discrete housings). As discussed above, in some examples all of computing device 200 as depicted in FIG. 3 may be contained in brushing apparatus 120 of FIG. 1A. Controller 110 may include interfaces 210, processor 220, and memory 230. Controller 110 may include any number or amount of interface(s) 210, processor(s) 220, and/or memory(s) 230.

Controller 110 may include components that enable controller 110 to communicate with (e.g., send data to and receive and utilize data transmitted by) devices that are external to controller 110. For example, controller 110 may include interface 210 that is configured to enable controller 110 and components within controller 110 (e.g., such as processor 220) to communicate with entities external to controller 110. Specifically, interface 210 may be configured to enable components of controller 110 to communicate with brushing apparatus 120, user devices 150, database 155, or the like. Interface 210 may include one or more network interface cards, such as Ethernet cards, and/or any other types of interface devices that can send and receive information. Any suitable number of interfaces may be used to perform the described functions according to particular needs.

As discussed herein, controller 110 may be configured to detect physical anomalies on a body. Controller 110 may utilize processor 220 to detect physical anomalies. Processor 220 may include, for example, microprocessors, digital signal processors (DSPs), application specific integrated circuits (ASICs), field-programmable gate arrays (FPGAs), and/or equivalent discrete or integrated logic circuits. Two or more of processor 220 may be configured to work together to detect physical anomalies of a body using brushing apparatus 120.

Processor 220 may evaluate and detect physical anomalies according to instructions 240 stored on memory 230 of controller 110. Memory 230 may include a computer-readable storage medium or computer-readable storage device. In some examples, memory 230 may include one or more of a short-term memory or a long-term memory. Memory 230 may include, for example, random access memories (RAM), dynamic random-access memories (DRAM), static random-access memories (SRAM), magnetic hard discs, optical discs, floppy discs, flash memories, forms of electrically programmable memories (EPROM), electrically erasable and programmable memories (EEPROM), or the like. In some examples, processor 220 may detect physical anomalies according to instructions 240 of one or more applications (e.g., software applications) stored in memory 230 of controller 110.

In addition to instructions 240, in some examples gathered or predetermined data or techniques or the like as used by processor 220 to detect physical anomalies may be stored within memory 230. For example, memory 230 may include information described above that may be stored in database 155, and/or may include substantially all of database 155. For example, as depicted in FIG. 2, memory 230 may include anomaly data 232.

Anomaly data 232 may include a plurality of contours, such as composite contours of physical anomalies such as ticks, lice, or other such unwanted injurious objects that brushing apparatus 120 may detect on a body. Anomaly data 232 may further include a plurality of historical contours, which may include contours of one or more users, such as moles of one or more users. In some examples, historical contours may further include scars, atypical bone structures or atypical musculatures, or the like. Anomaly data 232 may further include certain thresholds for respective contours. For example, anomaly data 232 may indicate that some contours need to be matched with a higher degree of accuracy and/or confidence to identify a match. Similarly, anomaly data 232 may include an amount that historical contours such as moles need to grow to satisfy an injurious classification threshold.

In some examples, anomaly data 232 may further include response tactics. For example, anomaly data 232 may include data on how to respond to the physical anomaly and/or how to avoid the physical anomaly going forward. In some examples, anomaly data 232 many include links to medical or scientific articles or websites that may provide further information for a user in how to respond to a detected physical anomaly. Controller 110 may respond some or all of these links along with a notification as sent to user as described herein.

Memory 230 may further include user data 234. User data 234 may indicate specific user devices 150 that are associated with certain users, and/or how the respective users would like to receive notifications (e.g., via text, email, pop-up messages, app notifications, etc.). Further, user data 234 may indicate a respective compression force 136 of the user, where some users like to press brushing apparatus 120 in relatively harder or softer during use. In some examples, user data 234 may include limbs of a body that a user prefers to scan. For example, user data 234 may indicate that some users prefer to scan substantially all of their bodies, while other users only want to scan their head. When directing a user to brush a body using brushing apparatus 120, controller 110 may consult user data 234 to identify how much of a body to brush.

Memory 230 may include analysis techniques 236 that controller 110 may use to identify an unexpected contour, match unexpected contours to contours of anomaly data 232 and/or match to contours of repositories 160 over network 165. For example, analysis techniques 236 may include such data analyzing techniques as NLP techniques, image recognition techniques, speech-to-text techniques, or the like. NLP techniques can include, but are not limited to, semantic similarity, syntactic analysis, and ontological matching. For example, in some embodiments, processor 220 may be configured to parse comments from scientific catalogues or the like in repositories 160 to determine semantic features (e.g., word meanings, repeated words, keywords, etc.) and/or syntactic features (e.g., word structure, location of semantic features in headings, title, etc.) of the scientific catalogues. Ontological matching could be used to map semantic and/or syntactic features to a particular concept. The concept can then be used to determine the subject matter. In this way, using NLP techniques, controller 110 may, e.g., identify a page of a scientific catalogue website as relating to a specific insect with a contour that matches an identified unexpected contour, and therein gather anomaly data 232 such as what a name of the insect, how to treat a bite from that insect, how to avoid that insect, and the like.

Similarly, analysis techniques 236 may include image recognition techniques such as pattern matching, shape identification, image recognition techniques, and/or object tracking techniques where images are received as a stream of images (e.g., as part of a video feed) to detect physical anomalies as described herein. Controller 110 may use these analysis techniques 236 to analyze captured images to identify unexpected contours, compare unexpected contours to composite contours and/or historical contours, or the like.

Figure 4:
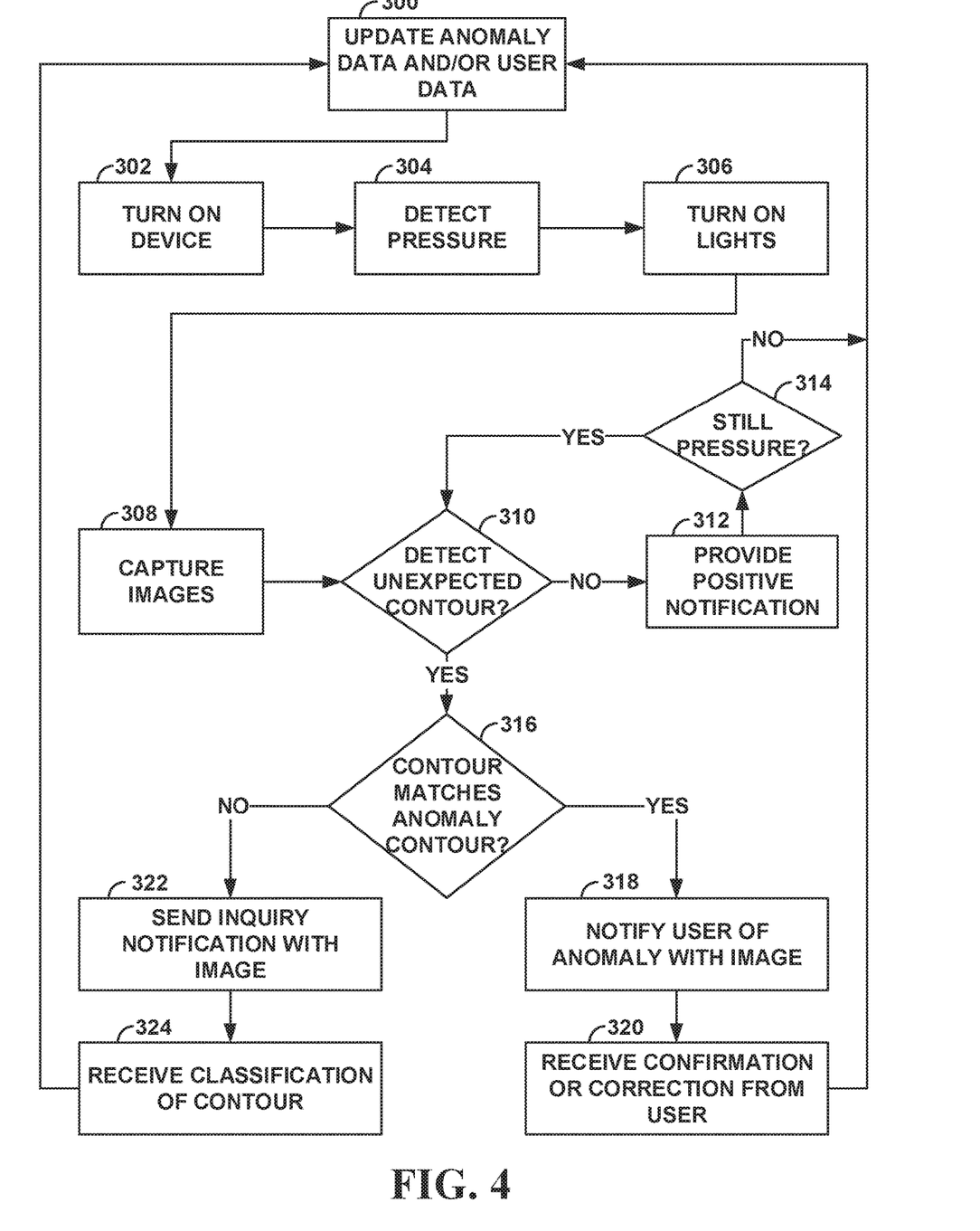
FIG. 4 depicts an example flowchart of detecting physical anomalies.

Controller 110 may detect physical anomalies according to many techniques. For example, controller 110 may detect physical anomalies according to the flowchart depicted in FIG. 4. The flowchart of FIG. 4 is discussed with relation to FIGS. 1A-1C for purposes of illustration, though it is to be understood that other systems may be used to execute the flowchart of FIG. 4 in other examples. Further, in some examples system 100 may execute a different method than the flowchart of FIG. 4, or system 100 may execute a similar method with more or fewer steps in a different order, or the like.

Controller 110 may update anomaly data and/or user data (300). Controller 110 may update this data as stored within database 155. Controller 110 may regularly crawl through online repositories 160 to identify new or updated anomaly data such as new response tactics. Further, controller 110 may update data such as existing composite contours of database 155, and/or create new composite contours in response to detecting articles about a new type of insect that may be an injurious physical anomaly for the user. For example, controller 110 may identify that a geographical location of a user (e.g., as gathered from user devices 150) indicates that the user is in a different region of the world in comparison to a normal location at which controller 110 monitors for and detects physical anomalies for the user. In response to this, controller 110 may search repositories 160 for physical anomalies related to this location, identifying one or more anomalies that have relationships with this region (e.g., a different species of lice or tick or the like that is native to the region) that are not currently in database 155, and add these anomalies and respective contours to database 155.

Controller may detect that brushing apparatus 120 is turned on (302). A user may turn on brushing apparatus 120 by pushing in power button 142 with at least a threshold amount of force. Once power is turned on, pressure sensors 130 may detect bristles 126 are compressed into head 134 with compression force 136 (304). Controller 110 may identify that pressure sensors 130 have identified the compression of bristles 126. In response to pressure sensors 130 detecting compression force 136, controller 110 may cause lights 124 to turn on (306) and cause one or more cameras 122 to capture images (308). In some examples, controller 110 may cause lights to turn on first, so that cameras 122 may adjust to the lighting condition. In other examples, controller 110 may cause lights to turn on and cameras to capture images at substantially the same time.

Controller 110 may analyze the captured images to determine if any unexpected contours are detected (310). Controller 110 may disregard images of hair and musculature and the like in monitoring for unexpected contours. In some examples, if controller 110 identifies that pressure sensors 130 have stopped detecting compression force 136, controller 110 may notify a user (e.g., where a user was not applying a strong enough force to ensure that cameras 122 are locating any potential anomalies within depth of field 140) using user device 150. As discussed herein, controller 110 may direct a user in where to engage brushing apparatus 120, including telling the user when sufficient information is gathered such that the user may move to another region as chosen by controller 110.

For so long as controller 110 does not detect unexpected contours, controller 110 may provide an ongoing positive notification to a user (312). For example, controller 110 may be directing a user to brush different areas of a body on an application interface on user device 150, and controller 110 may be doing so with a green background on the user interface to indicate positive results. Controller 110 may determine whether pressure sensors 130 are still detecting pressure from compression force 136, indicating that the user is still operating brushing apparatus 120 correctly (314). For so long as pressure sensors 130 are still detecting pressure, controller 110 may continue monitoring for unexpected contours (310). If controller 110 identifies that pressure sensors 130 are no longer detecting pressure of compression force 136, controller 110 may resume managing database 155 (300).

If controller 110 does detect an unexpected anomaly (at 310), controller 110 may determine whether the unexpected contour matches an anomaly contour (316). An anomaly contour may include a composite contour of database 155, a historical contour of database 155, a gathered contour of repositories 160, or the like. Where controller 110 matches the unexpected contour with such a contour, controller 110 may notify a user (318). Controller 110 may include an image of the unexpected contour along with the notification. In some examples, controller 110 may provide an ongoing video feed from cameras 122 to user device 150, such that a user may see a feed of the physical anomaly to confirm or reject an identification of the controller 110 of the physical anomaly.

Controller 110 may send the notification to the user along with recommended response tactics for the physical anomaly. In some examples, controller 110 may further include the anomaly contour that the unexpected contour was compared to for reference. For example, where the anomaly relates to potential growth of a mole, controller 110 may include a historical contour of the respective mole as an overlaid outline for reference.

Controller 110 may receive feedback from the user (320). Controller 110 may receive feedback that indicates that the user agrees with an injurious or benign classification of the user. For example, controller 110 may identify a new scab of a body as matching an anomaly contour of a tick, in response to which the user may respond back indicating that the unexpected contour is actually benign. In response to this classification, controller 110 may update anomaly data (300) to reduce the likelihood of such a false positive in the future. Further, though not depicted in FIG. 4 for the sake of clarity, in some examples controller 110 may continue monitoring for unexpected contours (310). For example, controller 110 may continue monitoring until controller 110 identifies that all areas of a body that a user has marked for searching have been searched for physical anomalies.

In other examples, controller 110 may detect an unexpected contour (at 310) and determine that the unexpected contour does not match available anomaly contours (at 316). In response to this, controller 110 may generate a notification for the user that includes the captured image and/or a video feed of the unexpected contour (322). Controller 110 may send this to a user device 150 of the user. Controller 110 may receive a classification of the unexpected contour (324). This classification may include whether or not the unexpected contour is injurious or benign. Where the classification includes an identifier such as a name for the unexpected contour, controller 110 may search repositories 160 for information (e.g., such as response tactics) related to the unexpected contour, and/or provide this information to user device 150. Controller 110 may update database 155 with such information as received from the user (300).

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method comprising:
   receiving, by a processor and from a camera secured to a head of a brushing apparatus, an image of a body from a predetermined distance away from the body as a result of bristles that define a length that is around the predetermined distance, wherein each of the bristles is configured to be resistant to bending and compressing more than a nominal amount when the brushing apparatus is engaged with a body, wherein the brushing apparatus is configured to make a depth of field of the camera static during engagement of the brushing apparatus as a result of each bristle of the plurality of bristles being resistant to bending and compressing;
   detecting, by the processor, an atypical contour of the image that indicates a physical anomaly by comparing the image to a plurality of images that all correspond to the depth of field; and
   generating, by the processor, a notification in response to detecting the atypical contour that indicates the physical anomaly.

2. The method of claim 1, further comprising:
   detecting, by the processor, a compression force applied to a bristle that exceeds a threshold force; and
   causing, by the processor, the camera to capture the image in response to detecting the bristle undergoing the compression force that exceeds the threshold force.

3. The method of claim 2, further comprising causing, by the processor, the camera to continue capturing subsequent images until the compression force no longer exceeds the threshold force.

4. The method of claim 3, further comprising analyzing, by the processor, each image of the subsequent images to determine if any image of the subsequent images indicates one or more of a plurality of physical anomalies, wherein the plurality of physical anomalies includes the physical anomaly.

5. The method of claim 1, wherein the comparing the image to the plurality of images that were all captured at the depth of field includes comparing, by the processor, the atypical contour with a composite contour of the physical anomaly,
   wherein detecting that the atypical contour indicates the physical anomaly includes the processor identifying that the atypical contour matches the physical anomaly within at least an identification threshold.

6. The method of claim 1, wherein the image is of a user and the comparing the image to the plurality of images that were all captured at the depth of field includes comparing, by the processor, the atypical contour with a historical contour of a mole of the user,
   wherein detecting that the atypical contour indicates the physical anomaly includes the processor identifying that the atypical contour is larger by at least a detection threshold in comparison to the historical contour.

7. The method of claim 1, further comprising:
   receiving, by the processor from a user associated with the image and in response to the notification, a benign classification of the physical anomaly;
   receiving, by the processor, a second image from the camera;
   detecting, by the processor, a second atypical contour of the second image that matches the atypical contour; and
   determining, by the processor in response to identifying the benign classification from the user for the atypical contour, to disregard the second atypical contour.

8. The method of claim 1, further comprising:
   receiving, by the processor from a user associated with the image and in response to the notification, an injurious classification of the physical anomaly;
   receiving, by the processor, a second image from the camera;
   detecting, by the processor, a second atypical contour of the second image that matches the atypical contour; and
   generating, by the processor and in response to identifying the injurious classification from the user for the atypical contour, a second notification that indicates the physical anomaly, wherein the notification includes the injurious classification.

9. The method of claim 1, wherein the notification is provided on a graphical display on a handle of the brushing apparatus such that the notification includes the image.

10. A computer program product, the computer program product comprising a computer readable storage medium having program instructions embodied therewith, the program instructions executable by a computer to cause the computer to:
    receive, from a camera secured to a head of a brushing apparatus, an image of a body from a predetermined distance away from the body as a result of bristles that define a length that is around the predetermined distance, wherein each of the bristles is configured to be resistant to bending and compressing more than a nominal amount when the brushing apparatus is engaged with a body, wherein the brushing apparatus is configured to make a depth of field of the camera static during engagement of the brushing apparatus as a result of each bristle of the plurality of bristles being resistant to bending and compressing;
    detect an atypical contour of the image that indicates a physical anomaly by comparing the image to a plurality of images that all correspond to the depth of field; and
    generate a notification in response to detecting the atypical contour that indicates the physical anomaly.

11. The computer program product of claim 10, wherein the comparing the image to the plurality of images that were all captured at the depth of field includes comparing the atypical contour with a composite contour of the physical anomaly,
    wherein detecting that the atypical contour indicates the physical anomaly includes the computer identifying that the atypical contour matches the physical anomaly within at least an identification threshold.

12. The computer program product of claim 10, wherein the comparing the image to the plurality of images that were all captured at the depth of field includes comparing the atypical contour with a historical contour of a mole of the user,
    wherein detecting that the atypical contour indicates the physical anomaly includes the computer identifying that the atypical contour is larger by at least a detection threshold in comparison to the historical contour.

13. The computer program product of claim 10, the computer readable storage medium further having program instructions embodied therewith that, when executed by the computer, cause the computer to:
    receive, from a user associated with the image and in response to the notification, an injurious classification of the physical anomaly;
    receive a second image from the camera;
    detect a second atypical contour of the second image that matches the atypical contour; and
    generate, in response to identifying the injurious classification from the user for the atypical contour, a second notification that indicates the physical anomaly, wherein the notification includes the injurious classification.

14. The computer program product of claim 10, wherein the notification is provided on a graphical display on a handle of the brushing apparatus such that the notification includes the image.

15. A system comprising:
a processor; and
a memory in communication with the processor, the memory containing instructions that, when executed by the processor, cause the processor to:
receive, from a camera secured to a head of a brushing apparatus, an image of a body from a predetermined distance away from the body as a result of bristles that define a length that is around the predetermined distance, wherein each of the bristles is configured to be resistant to bending and compressing more than a nominal amount when the brushing apparatus is engaged with a body, wherein the brushing apparatus is configured to make a depth of field of the camera static during engagement of the brushing apparatus as a result of each bristle of the plurality of bristles being resistant to bending and compressing;
detect an atypical contour of the image that indicates a physical anomaly by comparing the image to a plurality of images that all correspond to the depth of field; and
generate a notification in response to detecting the atypical contour that indicates the physical anomaly.

16. The system of claim 15, wherein the memory further includes instructions that, when executed by the processor, cause the processor to:
detect a compression force applied to a bristle that exceeds a threshold force; and
cause the camera to capture the image in response to detecting the bristle undergoing the compression force that exceeds the threshold force.

17. The method of claim 1, further comprising causing, by the processor, a graphical display on the brushing apparatus to indicate a portion of the body with which to engage brushing apparatus.

18. The method of claim 1, wherein the image is of a user and wherein the comparing the image to the plurality of images that were all captured at the depth of field includes comparing the atypical contour with a historical contour of a mole of the user, wherein detecting that the atypical contour indicates the physical anomaly includes identifying that the atypical contour is larger by at least a threshold in comparison to the historical contour; and
causing a graphical display on the brushing apparatus to provide the image of the mole as overlapped by the historical contour of the mole.

19. The method of claim 1, wherein the nominal amount is less than 1 millimeter.

* * * * *